United States Patent
Rosenfeld

(10) Patent No.: US 7,070,044 B2
(45) Date of Patent: Jul. 4, 2006

(54) SUTURE REEL DISPENSER WITH END OF SUTURE INDICATOR

(76) Inventor: David Rosenfeld, 11349 Isleta St., Brentwood, CA (US) 90049

( * ) Notice: Subject to any disclaimer, the term of this patent is extended or adjusted under 35 U.S.C. 154(b) by 164 days.

(21) Appl. No.: 10/228,903

(22) Filed: Aug. 27, 2002

(65) Prior Publication Data

US 2003/0025023 A1 Feb. 6, 2003

Related U.S. Application Data

(62) Division of application No. 09/576,980, filed on May 23, 2000, now Pat. No. 6,467,612.

(60) Provisional application No. 60/135,465, filed on May 24, 1999, provisional application No. 60/143,794, filed on Jul. 14, 1999, provisional application No. 60/143,795, filed on Jul. 14, 1999.

(51) Int. Cl.
A61B 17/06 (2006.01)

(52) U.S. Cl. ............ 206/63.3; 206/389; 242/563

(58) Field of Classification Search .......... 206/63.3, 206/380, 389, 398, 399, 414, 415; 242/160.3, 242/563, 812; 116/67 A, 200, 335, DIG. 41
See application file for complete search history.

(56) References Cited

U.S. PATENT DOCUMENTS

| | | | |
|---|---|---|---|
| 2,563,198 A | * | 8/1951 | Thalhammer .......... 206/398 |
| 3,648,949 A | * | 3/1972 | Berger et al. ........ 206/63.3 |
| 3,718,290 A | * | 2/1973 | Wright .............. 242/344 |
| 3,749,238 A | * | 7/1973 | Taylor .............. 206/63.3 |
| 3,876,068 A | | 4/1975 | Sonnino |
| 4,084,692 A | | 4/1978 | Bilweis |
| 4,893,764 A | * | 1/1990 | Juntunen ............ 242/586 |
| 4,901,663 A | | 2/1990 | De Luca |
| 4,947,276 A | * | 8/1990 | Meguro ............. 360/132 |
| 5,131,534 A | | 7/1992 | Brown et al. |
| 5,159,943 A | | 11/1992 | Richards et al. |
| 5,365,874 A | | 11/1994 | Dorfman |
| 5,392,903 A | * | 2/1995 | Sinn ................ 206/63.3 |
| 5,460,263 A | | 10/1995 | Brown et al. |
| 5,667,155 A | | 9/1997 | Cerwin et al. |
| 5,765,740 A | | 6/1998 | Ferguson |
| 5,911,829 A | | 6/1999 | Maksudian et al. |

FOREIGN PATENT DOCUMENTS

JP 09121099 A * 5/1997

* cited by examiner

Primary Examiner—Mickey Yu
Assistant Examiner—J. Gregory Pickett
(74) Attorney, Agent, or Firm—Berliner & Associates

(57) ABSTRACT

A dispenser for suture, including a suture reel on which the suture is mounted and an indicator that the suture is soon to be depleted. The indicator can be a visual marking on the suture, or it can be an audible and/or vibratory effect obtained by the dispenser housing interacting with the suture through one or more view ports or by interaction of a follower cam with the reel structure as the suture becomes depleted.

1 Claim, 11 Drawing Sheets

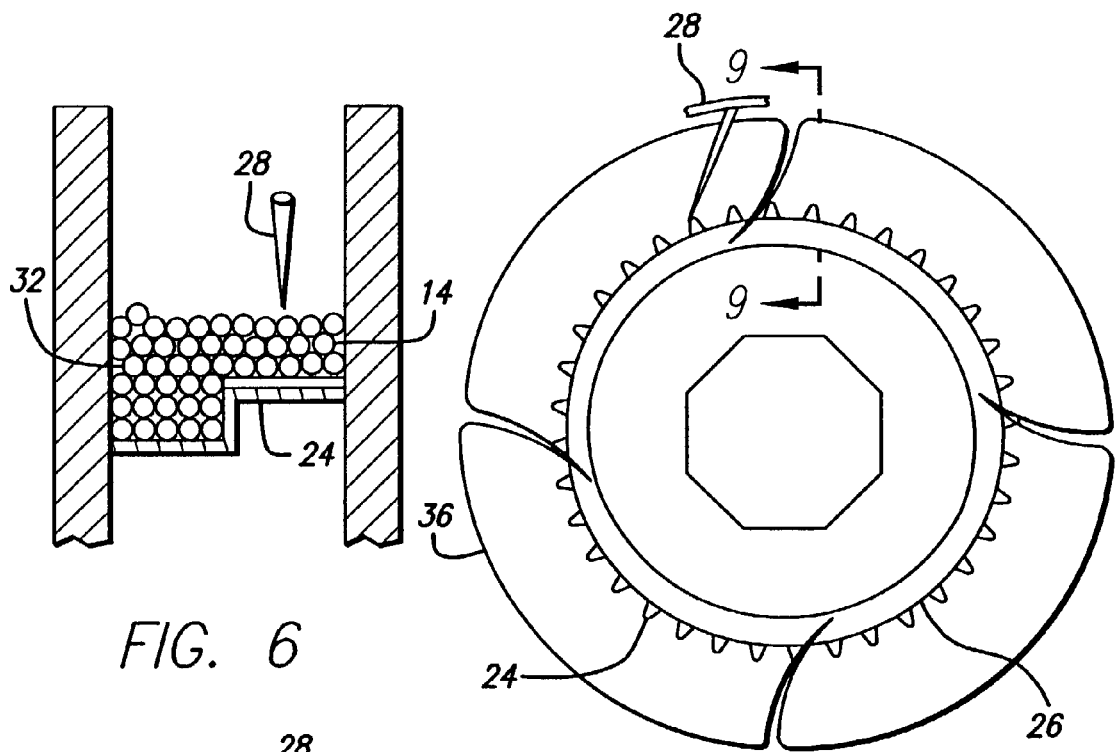
FIG. 6
FIG. 7
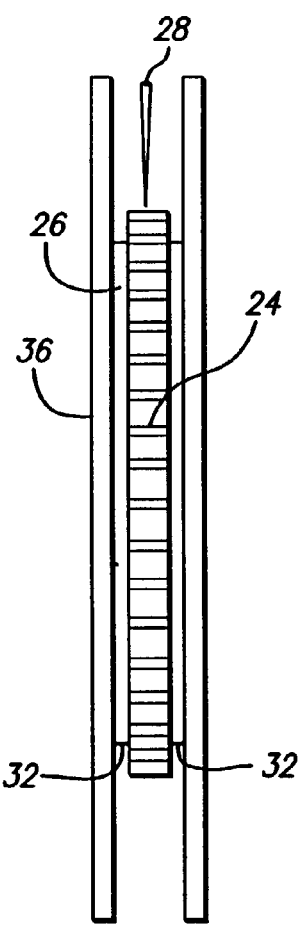
FIG. 8
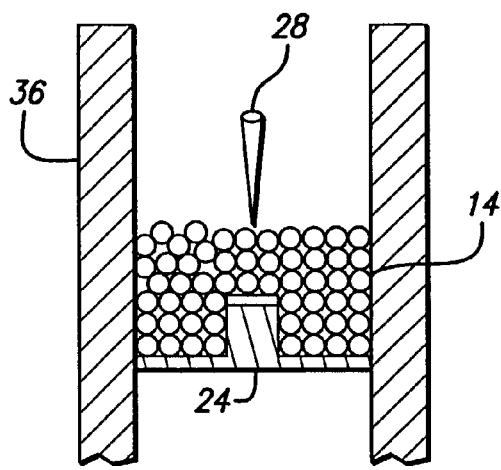
FIG. 9

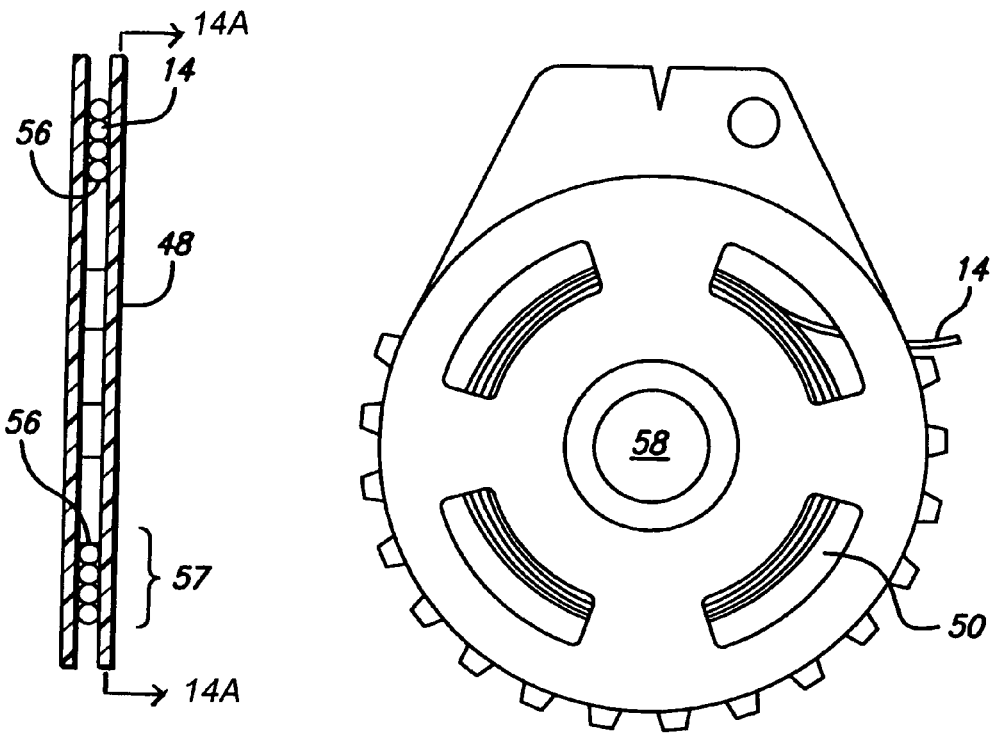
FIG. 14
FIG. 15
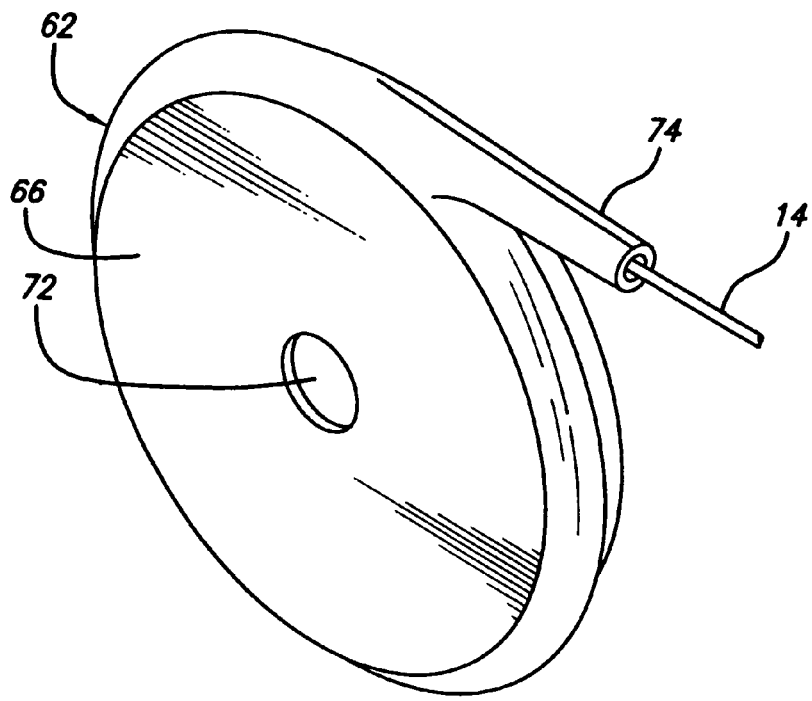
FIG. 16

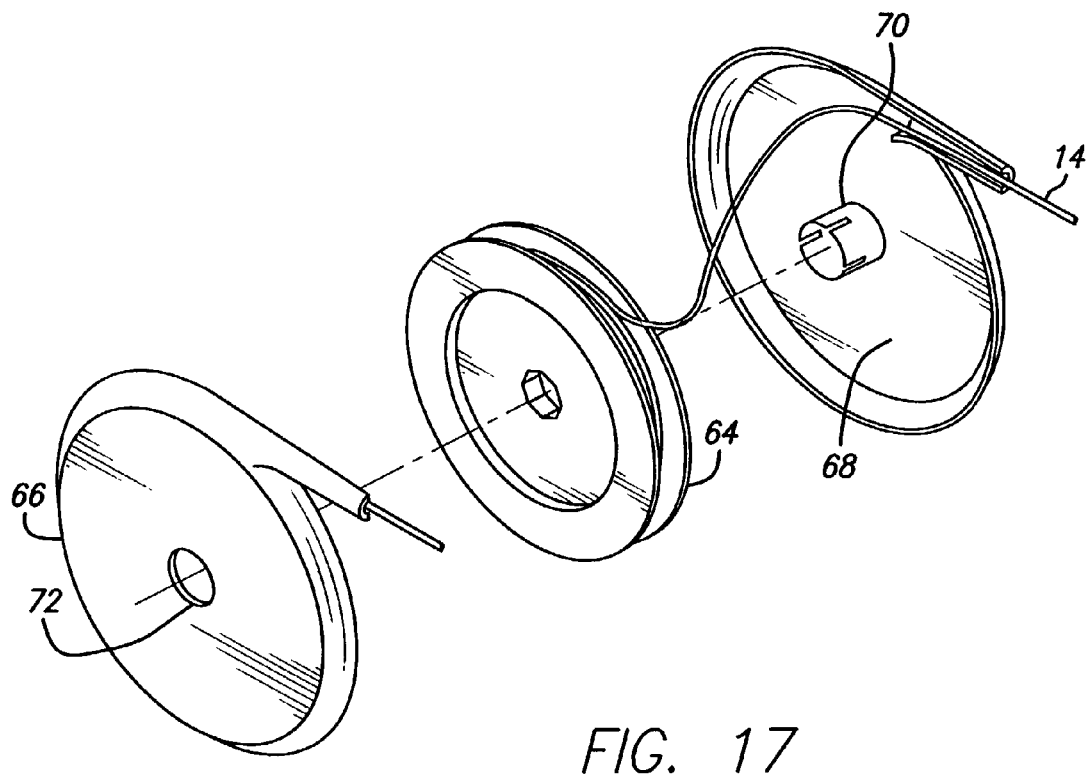
FIG. 17
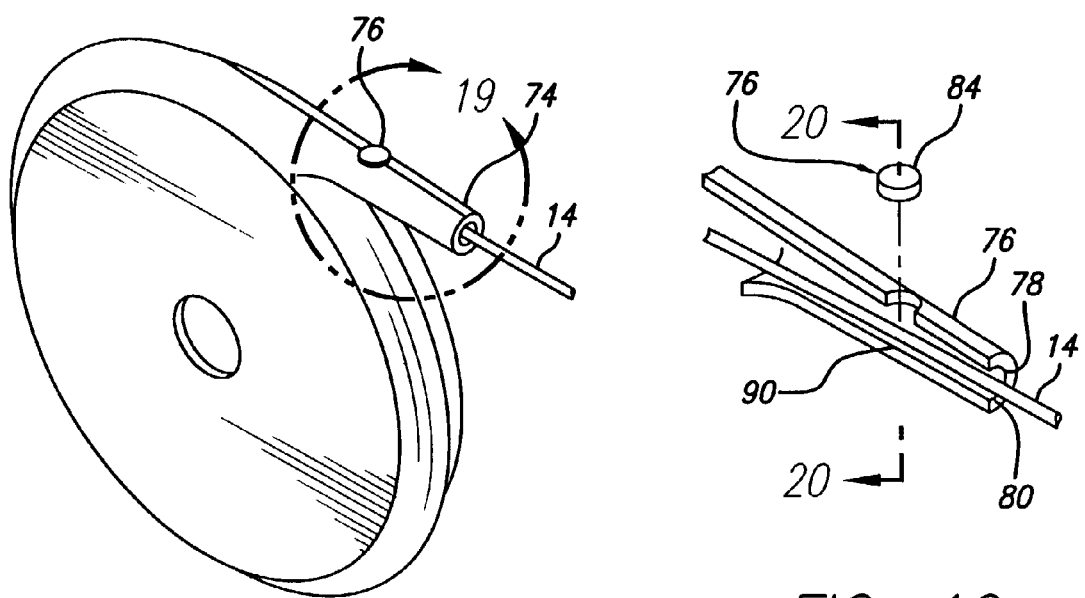
FIG. 18
FIG. 19

SUTURE REEL DISPENSER WITH END OF SUTURE INDICATOR

CROSS REFERENCE TO RELATED APPLICATIONS

This application is a divisional of application Ser. No. 09/576,980 filed May 23, 2000, now U.S. Pat. No. 6,467,612 and claims the benefit of Provisional Patent Application Nos. 60/135,465, filed May 24, 1999 and 60/143,794, filed Jul. 14, 1999, and 60/143,795, filed Jul. 14, 1999.

FIELD OF THE INVENTION

The field of the invention relates to suture reel dispensers and suture.

BACKGROUND OF THE INVENTION

For surgeons, an emphasis on working safely and quickly in the operating theatre is of paramount importance, as extra time spent during surgery can be dangerous to the patient. A patient remaining anesthetized for longer than is necessary endures more intraoperative and postoperative risks, including: atelectasis (lung collapse) which can lead to pneumonia, deep venous thrombosis (clots in the veins of the legs), pulmonary embolism (clots that leave the veins of the legs and lodge in the lung veins), stroke, myocardial infarction (heart attack), and even death. Manufacturers of equipment used during surgery strive to improve efficiency and safety.

Another major concern in the medical field is cost effectiveness. Wasting sterile instruments and equipment can be quite expensive. Any increase in cost a hospital accrues is translated into an inflated charge to individual patients. The future of medicine looks toward cost efficiency and patient safety.

By understanding the dynamics of the operating theatre, one realizes the importance of having materials and instruments ready prior to the surgeon asking for them. The basic allotment of people in the operating room involved with the surgery includes: (1) the patient; (2) the anesthesiologist; (3) the scrub nurse (sterile); (4) the surgeon (sterile); (5) a surgical assistant (sterile); and, (6) the circulating nurse (non-sterile). All instruments and materials, that the scrub nurse and the surgeon handle, must be sterile. All equipment is packaged so that while the outer cover is non-sterile, the inner package is sterile. Most equipment necessary to do a procedure is opened prior to an operation. Therefore, it is sterile and ready to use.

Moreover, in order to save money, the amount of equipment opened prior to the start of each individual operation is standardized. An estimate is made of how much material a surgeon will use during an individual procedure and the set-up is arranged so that there is, presumably, just enough material to complete a surgery. Very often during a surgery, the surgeon uses more material than what was pre-opened, requiring the surgeon to ask for more material. It is the circulating nurse's responsibility to acquire the necessary material and/or equipment, and then pass it to the scrub nurse in sterile fashion. Since the scrub nurse, the surgical assistant, and the surgeon are to remain sterile, only the circulating nurse is allowed to retrieve the necessary material and/or equipment. This makes the surgeon dependent upon the circulating nurse. Because the circulating nurse has other responsibilities, the surgeon is constantly waiting for her/him to retrieve the necessary material and/or equipment and hand it to the scrub nurse. These delays can be very lengthy. Suture, i.e., surgical thread, is one such material that the surgeon most often asks for.

Suture is a necessary material used to tie tissue and blood vessels in order to prevent hemorrhage (bleeding). Suture comes either fastened to a needle for sewing tissue, or free of needles used to tie clamped tissue. Sutures are made of different thickness, qualities (dissolvable, biodegradable, non-dissolvable), and solid colors (black, off-white, purple and others). Suture, not attached to needles, is packaged either wrapped around a spool (suture reel dispenser) or as multiple individual ties.

Suture reel dispensers were created to increase the efficiency of dispensing suture. Spooled suture allows the surgeon to draw suture from a larger one-unit supply each time a suture is needed, rather than reaching for individual ties, of limited length. The surgeon holds the suture reel dispenser in one hand and pulls the suture to the length needed with the other hand, and then ties the tissue or vessel. The surgical assistant then cuts the suture. With the reel remaining in the surgeon's hand, this procedure can be done over and over without needing to look away from the wound until the reel runs out of useable suture.

The medical supply companies that sell suture reels, wrap a standard amount of suture around the inner spool. A major disadvantage of prior suture and reel dispensers, is that the surgeon never knows how many ties he or she will have per reel so that he or she does not know when the suture will end until the last piece of useable suture is pulled out of the reel. Very often, the surgeon is left holding a piece of suture, which is too short to use. The surgeon must then ask for another suture reel, which often results in an unacceptable delay before another sterile reel is available for the surgeon. This delay can be detrimental to the patient's health. One way to prevent this dilemma would be to place more suture reels on the instrument table prior to surgery. Since it is never really known how much suture will be used during any individual operation; and, since any exposed, but, unused suture must be disposed of, this wasted material adds up to an increase in the cost of health care.

One would think that a suture reel (spool) made of clear plastic would enable the surgeon to look directly at the suture reel and, thereby, have an indication of the amount of suture remaining on the suture reel. This concept, in actuality, is not feasible for several reasons. First, the width of the prior suture reel is many times the diameter of the suture. As the suture is originally loaded around the suture reel spool, it wraps horizontally and then stacks vertically to a distance of about 2 mm, measured from the center of the suture reel. As the suture is drawn from the dispenser, the suture reel rotates in reverse to the way the suture was loaded; horizontally, approximating one layer at a time, thereby vertically reducing the amount of previously loaded material. Several revolutions of the suture reel decreases the vertical distance of the suture from the center of the suture reel by a miniscule and practically unnoticeable amount. In order to observe the suture winding down, the surgeon would have to continuously look at the suture reel when pulling the suture out of the suture reel dispenser; by which action, would take the focus of the surgeon off the operation and, therefore, would be unacceptable. In reality and actual practice, surgeons keep his or her focus and attention directly on the operation and, therefore, looks away from the wound as little as possible.

Another disadvantage of the prior suture reel dispenser is difficulty in handling it. A suture reel dispenser must operate in a manner that allows the suture reel to rotate smoothly and freely, without a need to place undue tension on the suture in order to draw it from the suture reel dispenser. The prior suture reel dispenser contains a suture reel attached to a reel housing and is constructed so that the reel housing does not completely cover the suture reel. The apparatus is quite small, which makes it difficult to hold the suture reel dispenser without the surgeon's fingers touching the suture reel. Moreover, surgeons wear gloves, which makes this task even more arduous. Friction on the suture reel from the surgeon's fingers both increases the force necessary to pull the suture out of the suture reel dispenser and prevents the suture reel from turning freely. For example, at times, while the surgeon is pulling suture from the dispenser, the whole apparatus can become dislodged from the surgeon's grasp, caused by an abrupt stopping force or tension, when the suture reel does not rotate smoothly. Furthermore, the required smooth, rotating action of the suture reel, on its built-in axle, can easily be inhibited by any slight increase in friction on the reel body or by the lodging of the suture in the suture reel or dispenser, or by a combination of several of these factors. Any disruption of a normal, smooth dispensing action of the suture, results in the surgeon's attention being diverted away from the operating field; thereby causing an unacceptable delay and is, most always, quite frustrating to the surgeon.

Lastly, another disadvantage of prior suture reel dispensers is that some suture needs to be moist, however, housing mechanisms are developed to house dry suture. Liquid can be placed into the housing but there is no guarantee that this will continuously be in contact with the suture. Therefore, by providing a means of placing a device onto the housing which is connected to the spool and spins freely with the spool; thus, not effecting the mechanism of the reel dispenser.

BRIEF SUMMARY OF THE INVENTION

The foregoing difficulties and disadvantages are overcome by the present invention, which provides methods, material and apparatuses including a suture reel dispenser mechanism. The present invention first proceeds by providing means to enable a surgeon to discern when the end of a suture reel is near. The indicia can be a visual marking on the suture, or it can be an audible and/or vibratory effect. Alternatively, or in addition, the horizontal extent of the wrapped and stacked suture is limited so that the suture is wound with a greater vertical extent, enabling the surgeon to more easily determine when the end of the suture is near.

Still another embodiment of the present invention provides a housing method and mechanism for the suture reel dispenser mechanism.

Yet, another embodiment of the present invention provides alternative methods and mechanisms for housing the suture dispenser and prevent the suture from unwinding.

Lastly, another embodiment of the invention provides a means to keep the suture moist.

In summary, a suture reel and suture reel dispenser and housing mechanism combination are provided that are easy to handle, operate dependably and reliably, and enable surgeons to immediately know when he is about to run out of suture. This invention eliminates delays in obtaining sufficient suture, and as a result, one need not overstock suture at the surgeon's station, thereby reducing waste.

Visual Indicia On Suture. In one embodiment of the invention, suture utilizing the present invention is imbedded, marked, tagged or applied with visual indicia, which can be, e.g., a different color on the final end, or solid, alternating vertical, alternating diagonal, striped, alternating dotted, hatched patterns, or a combination of any pattern, mixed with one another, or placed sequentially next to one another. The indicia is stationed at the end of the reel loaded suture immediately adjacent to and/or anchored to the spool body, for a specified length from the suture end, differentiating it from the suture ahead of the indicia. The indicia thereby indicates that a predetermined quantity of reel loaded suture is coming to an end. The remaining suture will be long enough, from the point of differential indicia (identification point) to the physical end of the suture, for the surgeon to request more suture, as needed, and continue working. The surgeon's eyes rarely leave the wound, therefore, he/she is always looking at the suture as the material comes out of the dispensing apparatus, a viewpoint which is generally within the surgeon's same scope of view of the wound. When the suture changes to visual indicia, the surgeon will immediately know that the suture is near the end of the reel loaded quantity of suture and can immediately call for another suture reel. During the time it takes for the circulating nurse to obtain the new reel, the surgeon can continue to work with the remaining useable indicia marked suture.

Audible and/or Vibratory Indicia. In another embodiment of the invention, a suture reel dispenser is provided that indicates when the suture is nearing its end by making a noise, a vibration or both. The suture reel dispenser is constructed with a plurality of nibs or other similarly functioning device, which can be of different designs and configurations, and which, at a specified length of suture, will cause an audible indicator, a vibratory indicator, or both, to signal the surgeon that the supply on the reel of suture is coming to an end. When the suture reel begins making a noise or causes a vibration, the surgeon will know that the suture is coming to its end, without looking away from the wound. The surgeon can immediately call for another reel and during the time it takes for the circulating nurse to obtain the new reel, the surgeon can continue to work with the remaining useable suture.

View Windows In the Suture reel and/or Housing. In this embodiment, one or more view windows (which can also be called ports) are placed in the suture reel and/or the suture reel housing, which allow the surgeon to simultaneously observe the remaining amount of useable suture on the suture reel and easily approximate when the wound suture will be coming to its end. By quick observation of the suture through on or more viewing windows, the surgeon, will, by changes of visual indicia within the background of the view window, immediately know that the suture is nearing its end.

In order for a view window to function properly, one needs to change the manner of stacking the suture on the reel. The diameter of prior suture reels are extremely wide relative to the width of the suture itself and preclude the use of one or more view windows. In accordance with another embodiment of the invention, the suture reel is designed and constructed to accommodate the specific diameter of any suture, which forces the suture to load around the suture reel hub in a radial fashion, one suture diameter wide, creating a uniform stacking effect. Therefore, when the surgeon draws the suture off the suture reel, each revolution of the suture reel results in the reduction of the loaded suture, sequentially, by one suture diameter (one layer being equivalent to one suture diameter). The surgeon can immediately observe this change through an integral view window. In a further embodiment, the background of the view window changes near the end of the suture, which is revealed when the suture winds down.

Since the surgeon's eyes rarely leave the wound, and since the suture reel dispenser is in his/her hand, within close proximity to the wound, he/she can easily look at the view window in or on the suture reel or suture reel housing. This embodiment can be provided as the sole indicia or it can be provided along with the visual, audible and/or vibratory indicia referred to above. When the view window changes visual indicia, the surgeon will know that the suture reel is near the end of useable suture. When the surgeon first notices the suture reel is near the end of useable suture, he or she can immediately call for another suture reel. During the time it takes for the circulating nurse to obtain the new suture reel, the surgeon can continue to work.

Suture Dispenser. In still another embodiment of the invention, the suture reel is encased within an enclosed suture reel housing. The suture exits through an opening within the suture reel housing. Th exit port of the enclosed suture reel can be used as an instrument to help place suture around other instruments.

However, with the suture reel completely enclosed within the reel housing, it can not be stopped by friction created by the surgeon's fingers. The suture reel, therefore, continues to turn freely and smoothly until the reel dispenses all of the contained suture. A disadvantage of prior suture reel dispensers is the inability of the surgeon to prevent the suture from coming out of the housing while trying to manipulate the suture. For example, when the surgeon is trying to place the suture around clamps or when he is tying knots with the suture. When pulling the suture in order to tie a knot, the free end of the suture is held in one hand, while the other end of the suture contained within the suture reel mechanism is held within the opposite hand. Hence, when pulling the free end of the suture during this manipulation, the suture continues to unwind from the suture reel dispenser. Therefore, by creating a devise/apparatus on the suture reel dispenser that when depressed will prevent the suture reel from spinning, the suture reel dispenser can be used to create tension on the suture in order to help place the suture around the clamps and help tie knots.

A mechanism to manually prevent the suture from unwinding. This embodiment of the invention creates a devise/apparatus on the enclosed suture reel dispenser that when depressed will prevent the suture from leaving the suture reel housing mechanism. It involves placing a device onto the housing which is connected to the spool and spins freely with the spool. The device has a flange or arm which can be raised in order to rewind excess suture. When not needed for re-winding, the flange or arm can be laid flat so as to not interfere with the smooth circular motion of the spool as suture is pulled from the suture. Furthermore, since the mechanism is attached to the spool, the user can place direct pressure on the mechanism in order to prevent the suture from unwinding. This tension is useful when placing suture around clamps, and when tying suture.

A housing mechanism for the suture reel mechanism. This embodiment of the invention, creates a partially enclosed suture reel, where the spool is exposed in order to give the user the ability to apply pressure directly to the spool when needed such as to tie suture. The spool is not exposed, although it has the same exit design as enclosed suture reels known to the art.

A mechanism to keep the suture moist. This embodiment of the invention places a sponge-like substance within the exit site of the suture reel housing, or on a cam placed within the housing if feasible. Both of these structures are in constant contact with the suture and both can be impregnated with fluid to keep the suture moist at all times.

In each of the embodiments of the invention delays encountered with prior systems become negligible or non-existent, being supplanted by manageable, cost reducing methodologies. Moreover, only the amount of suture needed is used. This invention both increases patient safety by decreasing the time in the operating room, and directly contributes to reducing the cost of surgery by decreasing the amount of wasted suture and increasing the efficiency of the operating staff.

BRIEF DESCRIPTION OF THE DRAWINGS

FIG. 6 is an enlarged cross-sectional view of a portion of the front and rear walls and hub of the suture reel of FIG. 3, showing its follower and cam with suture wound on the hub and cam surfaces;

FIG. 7 is an elevational front view of a suture reel formed with a follower cam and nibs therefore, in accordance with another embodiment of this invention;

FIG. 8 is an elevational side view of the follower and cam of FIG. 7, providing an audible/vibratory signal in accordance with this embodiment of the invention;

FIG. 9 is an enlarged cross-sectional view of the follower and cam, taken on line 9—9 of FIG. 7, shown with suture wound on the hub and cam surfaces;

FIGS. 14 and 14A are, respectively, an elevational side view of the suture reel of FIG. 12, taken on line 14—14 of FIG. 12, showing suture wound in single file on the hub surface, and an elevational view of the rear wall of the suture reel of FIG. 12, taken on line 14A—14A of FIG. 14, showing a color change thereon;

FIG. 15 is an elevational front view of a suture reel formed with windows serving as view ports placed in the housing mechanism in its front wall in accordance with another embodiment of this invention in which the hub rotates while the front and rear walls are held stationary;

FIG. 16 is a perspective view of a dispenser housing encasing a freely spinning suture reel in accordance with another embodiment of this invention;

FIG. 17 is an exploded view of the embodiment of FIG. 16 showing the housing, suture reel and suture;

FIG. 18 is a perspective view of a dispenser housing encasing a freely spinning suture reel in accordance with another embodiment of this invention that includes a retention mechanism in the dispenser housing exit neck to selectively prevent suture from exiting the dispenser;

FIG. 19 is an exploded view of the retention mechanism in the dispenser housing neck of FIG. 18;

DETAILED DESCRIPTION OF THE INVENTION

Figure 1:
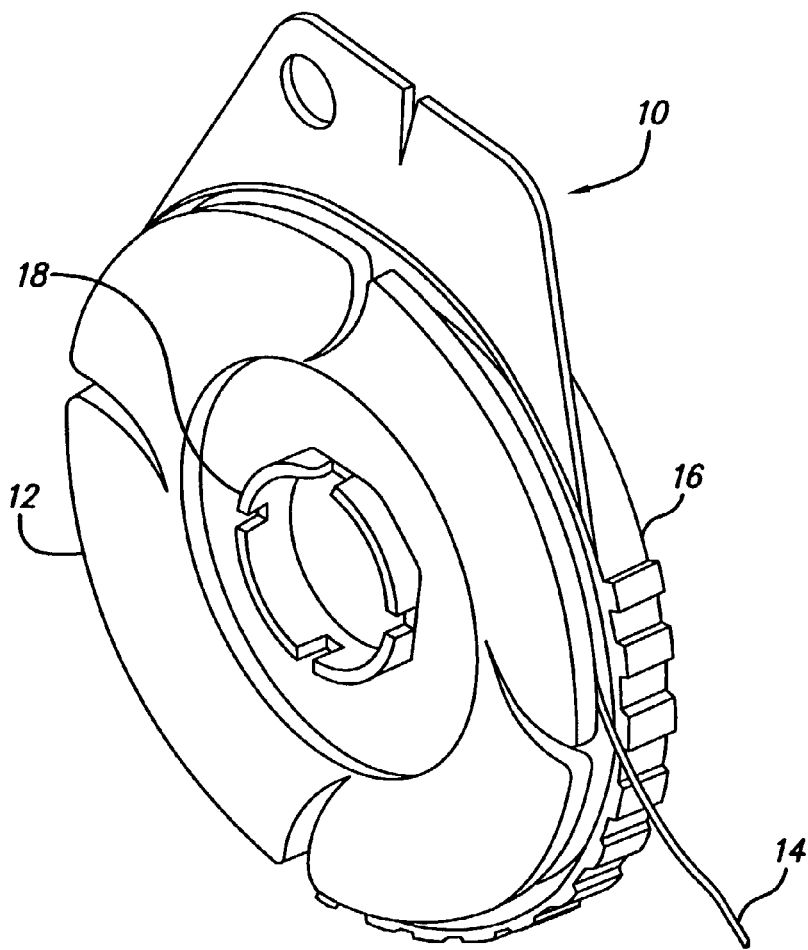
FIG. 1 is a perspective view of a prior art suture reel dispenser containing suture of this invention.

Referring to FIG. 1, a typical prior art suture reel dispenser is indicated at 10 and contains the suture reel 12, suture 14, and suture reel housing 16. The suture reel 12 sits within the suture reel housing 16 and rotates upon a boss 18 also contained within and attached to the suture reel housing 16. The suture 14 is loaded onto the suture reel 12 and when pulled unwinds from the suture reel 12 as it rotates on the boss 18.

Figure 2:
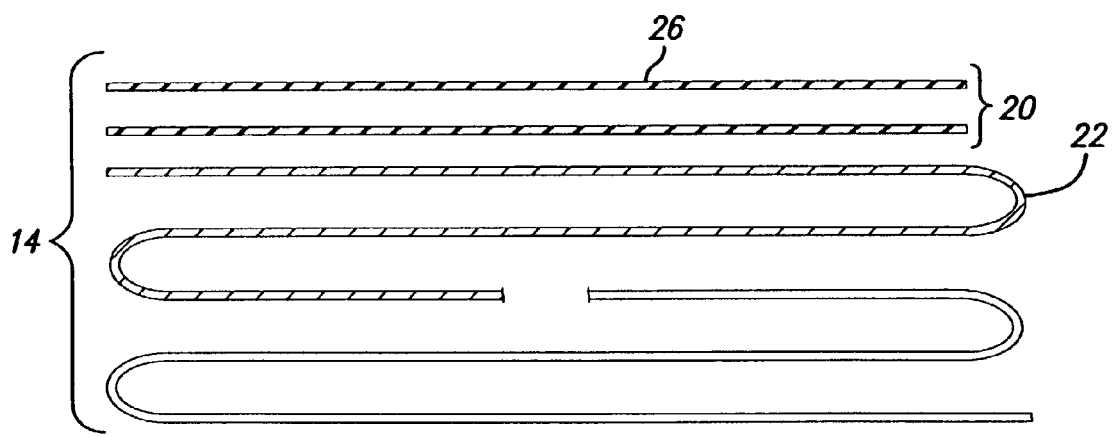
FIG. 2 is a plan view of a length of suture having visual indicia in accordance with this invention.

Referring to FIG. 2, an end portion 20 the suture 14 is marked with visual indicia 22 of a different appearance with respect to the major portion of the suture 14 which has been previously unwound from the suture reel 12. The difference in appearance can be based on a pattern that is solid, alternating vertical, alternating diagonal, striped, alternating dotted, hatched or a combination of any pattern including ones not listed above. More than one pattern can be used. The combination of patterns can be mixed with one another, or placed sequentially next to one another. The indicia may be of different colors. The length of suture indicated by visual indicia 22 and/or 26 should be long enough to allow the surgeon to continue working for a period of time after noticing the change of visual indicia. This visual change in suture 14 will allow the surgeon to ask for another suture reel dispenser while continuing to work.

Thus there is provided an indicator that the suture is soon to be depleted, the indicator comprising an indicating segment of the length of suture having an appearance different from a prior segment of length of suture to be unwound from the suture reel dispenser 10, the indicating segment being located at a known or predetermined distance from an end of the suture 14 to indicate that the end length of suture 20 remaining within the suture reel dispenser 10 is nearing the end. The predetermined distance is preferably at least one twelfth to one quarter of the total length of the suture. One twelfth and one fourth comes from the ability to tie a piece of suture 10 inches long related to the total amount of suture contained within a suture reel dispenser. Some suture reel dispensers contain 98 inches and some contain 60 inches. Others still may vary relative to the two. Although it is possible to tie suture 14 at lengths less than 10 inches, a length of 10 inches appear to be the smallest length of suture one would need to easily manipulate and tie the suture 14.

Figure 3:
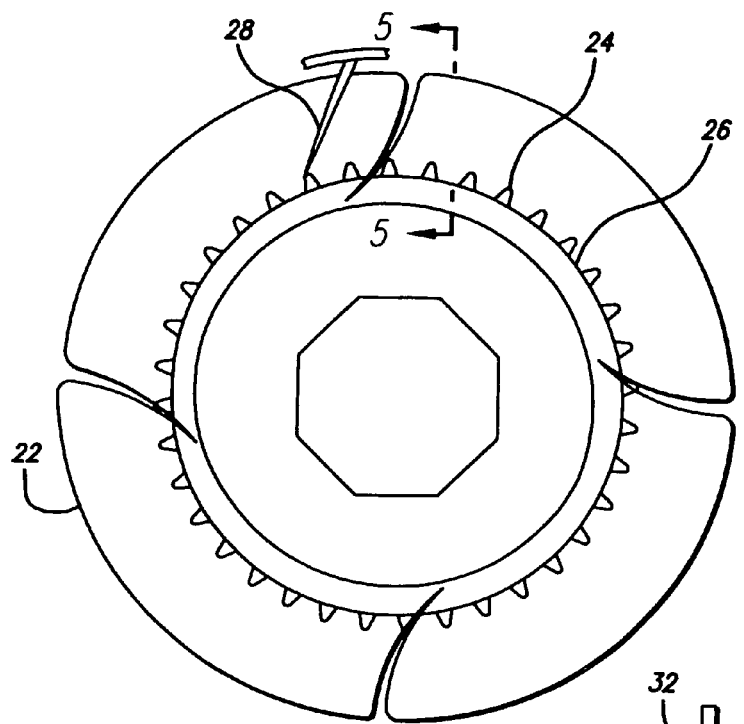
FIG. 3 is an elevational front view of a suture reel formed with a follower cam and nibs therefore, in accordance with another embodiment of this invention.
Figure 4:
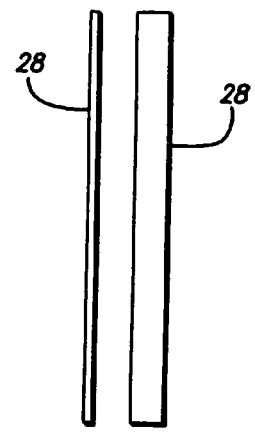
FIG. 4 depicts enlarged front and side views of the follower cam of FIG. 3.

Referring to FIG. 3, in accordance with another embodiment of this invention a suture reel 22 is provided containing nibs 24 or other apparatus, which are incorporated onto its base 26. The suture reel 22 sits within the suture reel housing 16 and spins upon the boss 18 (as in FIG. 1). A follower cam 28 is attached to the inside of circular side wall 16 of the suture reel housing 16. The housing and reel components can be advantageously formed by injection molding an injection moldable thermoplastic resin, e.g., a polyolefin such as polyethylene or polypropylene, a polyester such as polyethylene terephthalate, and the like. The follower cam 28 is formed from material that is stiff enough to make a noise when coming into contact with the nibs 24, but pliable enough to bend and accommodate suture 14 (which can be ordinary suture or suture having an indicator segment as described with respect to FIG. 2). For example the follower cam may be made from flat, thin spring metal such as spring steel, glued or secured by a grommet to the housing. Alternatively, it can be an extension of the housing and therefore formed of the same material as the housing. The suture 14 wraps around the suture reel 22 and covers its base 26 and nibs 24. The follower cam 28, shown enlarged in FIG. 4, has a flat, rectangular shape, preventing the cam 28 from falling between the suture 14.

Figure 5:
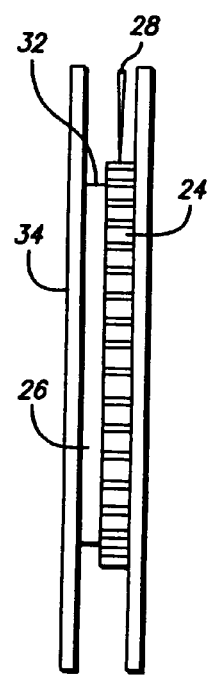
FIG. 5 is an elevational side view of the follower and cam, taken on line 5—5 of FIG. 3, providing an audible/vibratory signal in accordance with this embodiment of the invention.

FIG. 5 shows a side view of the suture reel 22 with the nibs 24 offset to one side and the follower cam 28 disposed on the same side. The nibs 24 are larger than the base 26 and therefore define a circular slot 32 between the front wall 34 and nibs 24. When the suture 14 is loaded onto the suture reel 22 it will first load within the slot 32. As the suture 14 continues to load onto the suture reel 22 it will fill the slot 32 forcing it to wrap horizontally across the nibs 24, as shown in FIG. 6. The follower cam 28 is carried on the suture 14 directly above the nibs 24 awaiting contact with the nibs 24 when the suture winds down to an end segment. As the suture 14 is pulled from the suture reel 22, the rows of suture 14 decrease to the level of the nibs 24.

The follower cam 28 is constructed and/or molded into the suture reel housing 16 with enough pressure to follow the suture 14 down to the nibs 24, and to create a noise and/or vibration when coming into contact with the nibs 24. The noise and/or vibration continues as the remaining suture 14 sitting in the slot 32 is pulled from the suture reel 22 causing it to rotate with the follower cam 28 in contact with the nibs 24. As is evident from FIG. 6, the follower cam 28 does not hinder the smooth movement of the suture reel 22 as the reel 22 spins. The suture reel nibs 24 can be made larger or smaller increasing or decreasing the slot 32 which will adjust how much suture 14 will remain as the follower cam 28 strikes the nibs 24.

A similar embodiment of the invention is shown in FIGS. 7, 8 and 9. The front view of the suture reel 36 has the same configuration as that of the suture reel 22 seen in FIG. 3. This suture reel 36 also contains nibs 24, which are incorporated onto its base 26, but the nibs 24 are disposed centrally on the base 26 so as that two circular slots 32 are defined, one on each side of the nibs 24. A follower cam 28 is attached to the inside of the suture, reel housing 16, as in the device of FIGS. 3 to 6, but is centrally disposed. Operation is otherwise the same. As the suture 14 is pulled from the suture reel 36, the rows of suture decrease to the level of the nibs 24, creating a noise and/or vibration when coming into contact with the nibs.

With either the single slot or dual slot configuration, the suture reel nibs 24 can be made larger or smaller increasing or decreasing the depth of the circular slots 32 so as to adjust how much suture 14 will remain as the follower cam 28 strikes the nibs 24.

Figure 10:
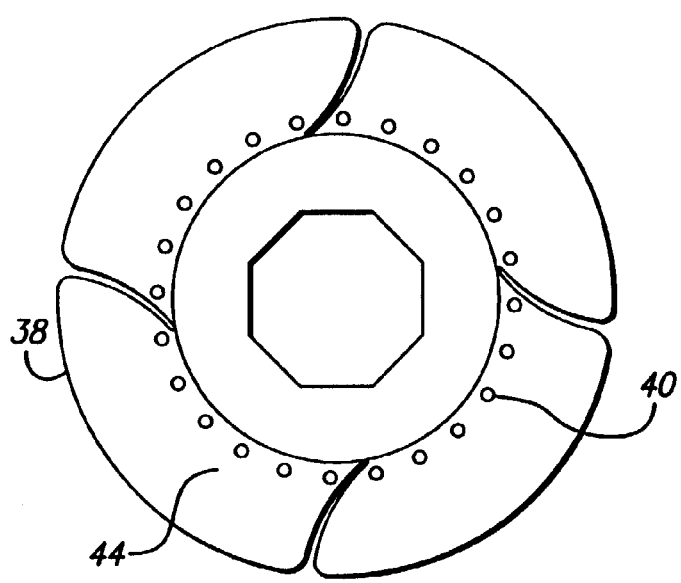
FIG. 10 is an elevational front view of a suture reel formed with nibs that interact with the terminal end of a line of suture to provide an audible/vibratory signal in accordance with another embodiment of this invention.
Figure 11:
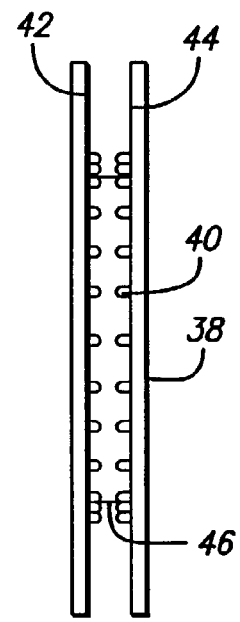
FIG. 11 is an elevational side view of the reel of FIG. 10, showing the nibs thereof in opposing relationship.

FIG. 10 shows a suture reel 38 with opposing sets of nibs 40, in circular arrays, attached to the inside of the front and rear walls, respectively 42 and 44, of the suture reel 38. Suture is loaded onto the suture reel 38 starting at its base 46. The suture winds inside the nibs 40 for a certain distance and then it passes through the nibs 40 and continues to be wound onto the opposing outer surfaces of the opposing sets of nibs 40. In use, when the suture nears depletion, the distance between the opposing nibs 40 is just wide enough to come into contact with the remaining suture to create a vibrating sensation and/or a noise as the suture makes contact with the nibs 40 while passing between them. As the suture is pulled from the suture reel 38, the suture reel 38 spins freely upon its axle as the suture that is wrapped on the outside of the nibs 40 is pulled out first.

The nibs 40 are set across from each other at a distance that approximates one suture width. As the suture comes into contact with a set of nibs 40, a small amount of resistance is placed onto the suture. As the suture reel 38 continues to spin, this resistance is rapidly repeated as the suture is pulled through the nibs 40. This intermittent resistance will be perceived as a vibration and/or a noise to the surgeon. The surgeon when feeling the vibration, or hearing the noise will know that the suture is coming to an end and can call for another suture reel. If enough suture is loaded onto the suture reel 38 prior to passing through the nibs 40, the surgeon can continue to work while waiting for another suture reel. By placing the nibs 40 further away from, or closer to, the suture reel base 46, the amount of remaining suture 14 can be varied.

Figure 14A:
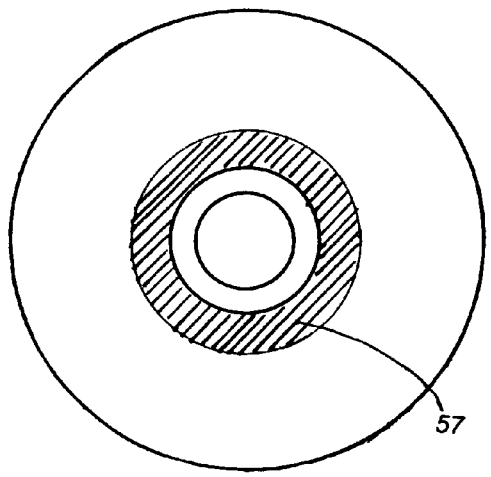
Figure 12:
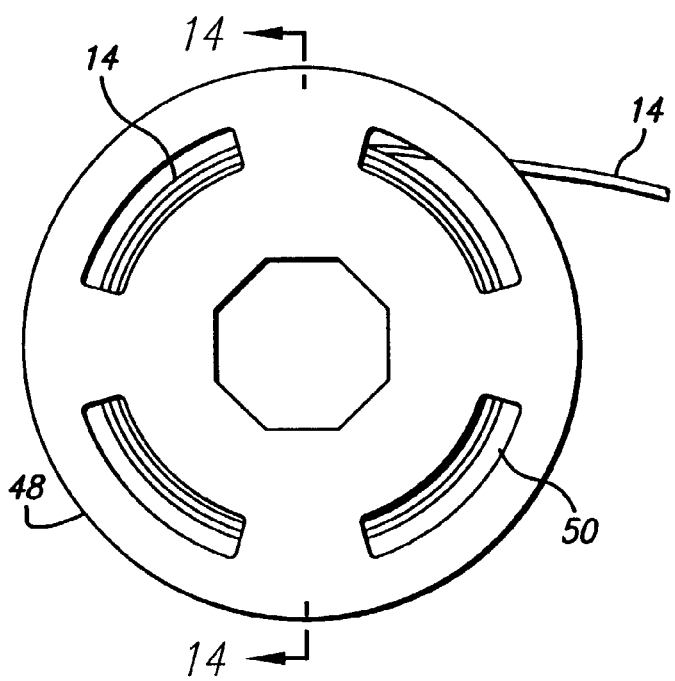
FIG. 12 is an elevational front view of a suture reel formed with windows serving as view ports in its front wall, the front and rear walls being integral with the hub of the reel, in accordance with another embodiment of this invention.
Figure 13:
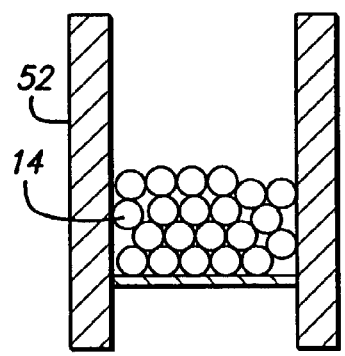
FIG. 13 is a cross-sectional view of a portion of the front and rear walls and hub of a prior art suture reel with suture wound on the hub surface.

Another embodiment is shown in FIG. 12. The suture reel 48 is constructed with one or more windows or view ports 50. The suture 14 can be seen within the view windows or view ports. FIG. 13 shows an enlarged side view of a prior art suture reel 52 where the suture 14 is wrapped horizontally and vertically. This makes using a window 50 difficult because it takes many revolutions to lower the suture 14 even one row. FIGS. 14 and 14A show, respectively a side view of a suture reel 54 and an elevational view of the rear wall of the suture reel 54 in accordance with another embodiment of the invention, having a width 56 substantially narrower than in the prior art suture reel 52. The suture 14 is wrapped vertically away from the base 42 of the suture reel 52. By loading in a vertical fashion, each rotation of the suture reel 52 will lower the suture 14 by one level, which can then be readily observed. A decrease in the supply of suture can be easily observed within one or more view windows 50. Furthermore, other changes of visual indicia, such as a change in the background of the view window 50, indicated at 57, can also be used to observe that the suture is coming to an end.

A plurality of view windows 50 are shown in FIG. 15, which depicts a suture wheel 54 as in FIG. 14, which spins on its axle 58, but wherein, in accordance with an embodiment of this invention, one or more view windows 50 are placed within the suture reel housing. The suture reel 54 is made out of a clear substance, such as clear polyethylene, in order to enable the suture 14 to be seen through the view window 14.

Referring to FIGS. 16 and 17, there is shown a suture reel dispenser 62 in accordance with another embodiment of the invention in which a suture reel 64 is encased within its encompassing opposing sides 66 and 68. The suture reel 64 rotates upon a boss 70 formed on one side 68 of the dispenser 62 which sits within a land 72 formed on the opposite suture reel dispenser side 66. The suture 14 extends through an elongate neck 74 to facilitate unhindered withdrawal from the suture reel. This configuration of an enclosed neck 74 also can act as an instrument to help facilitate the placement of suture 14 around other instruments. This construction allows the suture reel 64 to spin freely without touching the surgeon's fingers, preventing difficulties encountered with using a prior art suture reel 52, which consists of an exposed suture reel. Any of the above concepts and embodiments described in detail (i.e. visual indicia, nibs and follower cam, and view window, etc) can be used in conjunction with the structure of FIGS. 16 and 17.

Figure 20:
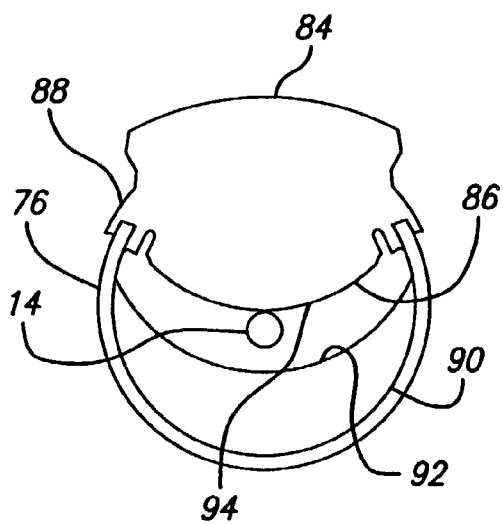
FIG. 20 is an enlarged, side cross-sectional view of the suture reel dispenser neck of FIG. 19, showing the retention mechanism in grater detail.

Referring to FIGS. 18, 19 and 20, still another embodiment of the invention is shown. Construction of the suture reel assembly of this embodiment is the same as that of the suture reel assembly of FIGS. 16 and 17, having a an elongate neck 74 through which suture 14 is fed from an internal reel. However, it also has a mechanism 76 on and inside and the neck 74 to prevent the suture 14 from being freely pulled from the suture reel. FIG. 19 shows an exploded, enlarged view of the circled region of FIG. 18 and FIG. 20 shows an enlarged plan view thereof. The mechanism 76 includes a flexible disk 78 with a central opening 80 through which the suture can be threaded. A plurality, e.g. four, slots 82 extend radially from the disk opening 80 which is smaller than the diameter of the suture 14, the slots 82 allowing the material of the disk 78 to bend to enable the suture to pass through the disk opening.

The mechanism also includes an outer stud 84 on the outer top surface of the neck 76 integrally connected to a smaller inner stud 86 through an opening 88 in the top wall of the neck 76, both studs 84 and 86 being larger in diameter than the top neck opening 86. A pad 90 is disposed on the bottom inside surface of the neck 76 having a top surface 92 confronting the bottom surface 94 of the inner stud 86. The suture 14 is disposed between the inner stud 86 and the pad 90, which sized and configured so that when the top stud 84 is pressed, it causes the inner stud 86 to be pressed into contact with the pad 90, thereby gripping the suture 14 between them. The inner stud 86 and pad 90 are formed from rubber or a rubber-like material, such as neoprene, or any soft, yielding, stretchable material can be used. The outer stud 84 can be formed of the same material as the inner stud 86 but is capped with a harder material such as a hard plastic or a metal. Preferably, while integral with the inner stud 86, the entire outer stud 84 can be formed of a harder material, one that will substantially retain its shape, such as a hard plastic or rubber, or metal.

The confronting outer pad and inner stud surfaces 92 and 94, are shaped to substantially mate, for example as concave and convex surfaces, respectively, as shown. The inner stud 86 is formed with a circular relief slot 96 near the neck opening 88 to allow the inner stud 86 to stretch as the outer stud 84 is pressed, thereby pinching the suture 14 between them and preventing the suture 14 from being freely pulled from the suture reel, while preventing trauma to the suture 14.

Figure 22:
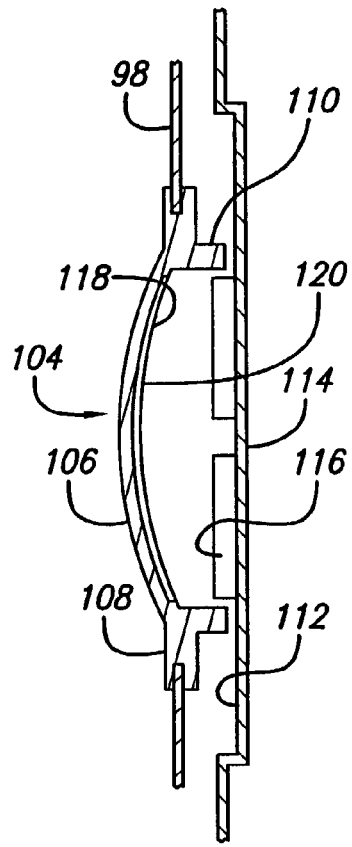
FIG. 22 is a detailed side view of mechanism in the dispenser of FIG. 21, taken on the line 22—22 of FIG. 21.
Figure 21:
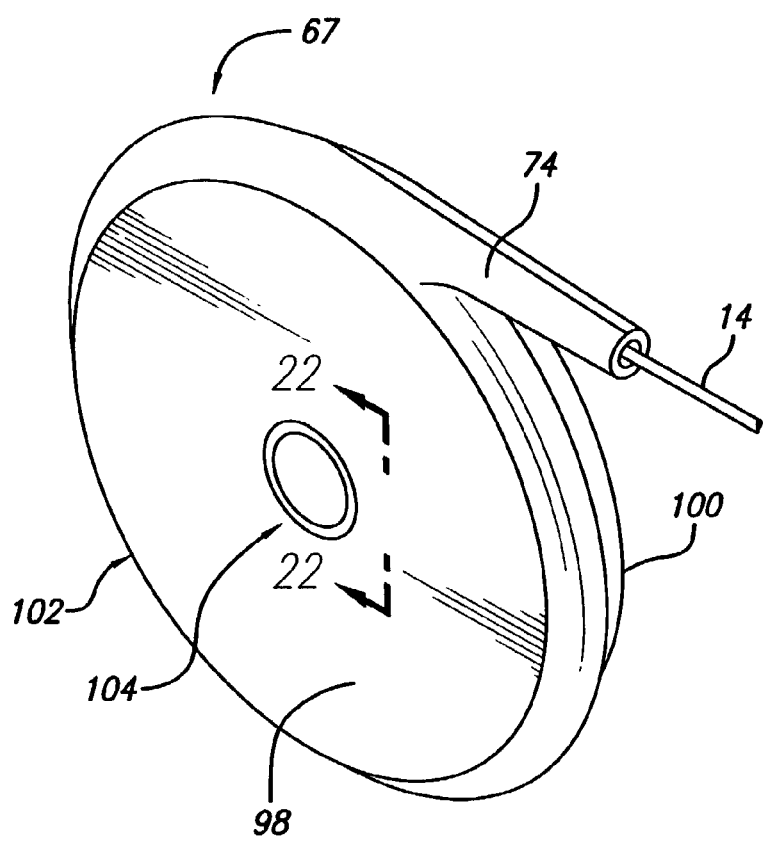
FIG. 21 is a perspective view of a dispenser housing encasing a freely spinning suture reel in accordance with another embodiment of this invention that includes a mechanism on a front wall of the dispenser housing to selectively prevent suture from exiting the dispenser.

Referring to FIGS. 21 and 22, there is shown another embodiment of the invention that also incorporates a suture restraining mechanism. Construction of the suture reel assembly of this embodiment is also the same as that of the suture reel assembly of FIGS. 16 and 17, having an elongate neck 74 through which suture 14 is fed from an internal reel. However, in this embodiment, the suture restraining mechanism 104 is located on the front wall 98 and/or the back wall 100 of the suture reel dispenser 102, for example centrally on the front wall 98, as shown. The mechanism 104 is formed as a button-like stud 106 disposed in an opening 108 therefor in the front wall 98 of the dispenser 102 and is integrally formed internally with a collar 110 which is sized to be spaced from, but closely adjacent, the confronting outer surface 112 of a suture reel 114 carried in the dispenser 102, a distance that will not interfere with rotation of the suture reel 114.

Whereas in the embodiment of FIGS. 16 and 17, the suture reel 64 rotates upon a boss 70 which has it distal end siting within a land 72 formed on the front wall of that dispenser 62, in this embodiment, the boss 116 that carries the suture reel 114 does not sit within a land. It extends a shorter distance than the boss 70 of the embodiment of FIGS. 16 and 17, but has sufficient extent to carry the suture reel 114.

The button-like stud 106 is formed of a flexible material such as neoprene rubber, or a semi-rigid thermoplastic material, and has a concave inner surface 118 facing the suture reel 114. The concave surface 118 is lined with a rigid member 120 having a matching convex surface, which can be made of rigid plastic or metal. The rigid member120 can be glued to the inner surface of the stud 106 or may be retained therein by somewhat flexing the member 120 and inserting it against the concave surface of the stud 106 to be retained by the stud collar 110.

In operation, the surgeon withdraws suture 14 from the neck 74 of the dispenser 102, which causes the internal suture reel to rotate on the boss 116 until a desired amount of suture has been obtained. He or she then simply presses the stud 106, which causes the collar 110 to bear against the outer surface of the suture reel 114 to stop its rotation. This will prevent the suture 14 from unwinding as the surgeon pulls on it. Thus, stopping the suture reel 114 from spinning is performed at the surgeon's discretion, which is particularly useful when placing the suture 14 around clamps, or when tying knots with the suture 14.

Although illustrated as being centrally located, the restraining mechanism 104 can be located anywhere on the dispenser 102 where the collar can impinge on the suture reel and stop it from rotating. The restraining mechanism 104 can also be located in more than one place on the dispenser 102 for easier accessibility and more than one restraining mechanism 104 can be placed on one suture reel dispenser 102. For example, the restraining mechanism 104 can be placed on both sides of the same suture reel dispenser 102 so that it can be easily operated when held in either hand, or as illustrated below, it can be placed on a side wall of the dispenser. The restraining mechanism 104 can also be of many shapes and sizes.

Figure 23:
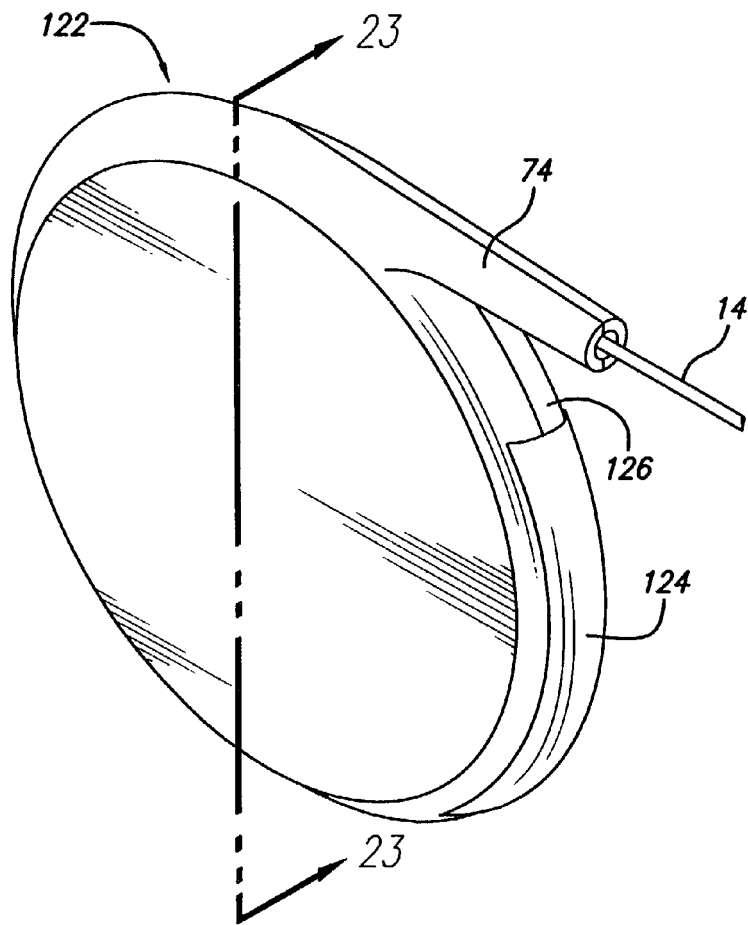
FIG. 23 is a perspective view of a dispenser housing encasing a freely spinning suture reel in accordance with another embodiment of this invention that includes a mechanism on a side wall of the dispenser housing to selectively prevent suture from exiting the dispenser.
Figure 24:
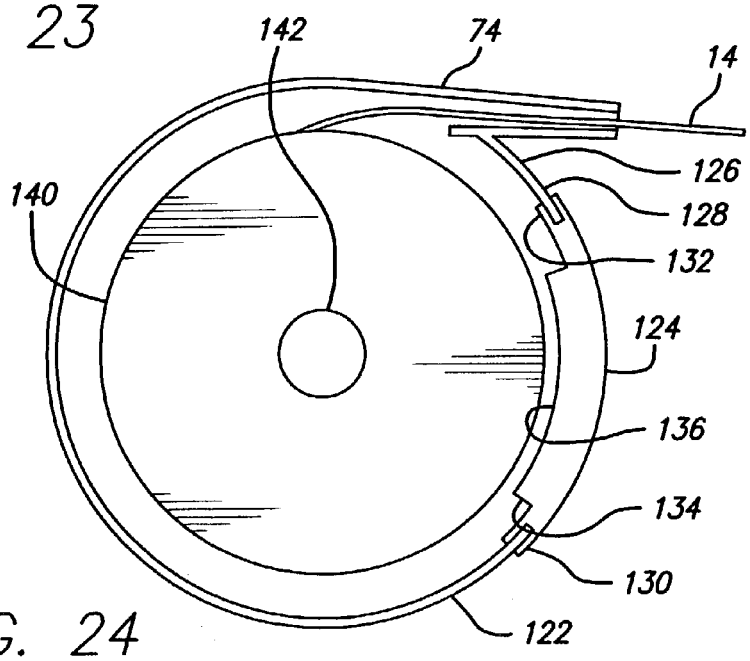
FIG. 24 is a detailed side view of mechanism in the dispenser of FIG. 23, taken on the line 24—24 of FIG. 23.

Referring to FIGS. 23 and 24, a suture reel dispenser 122 is shown having the same general construction of the suture reel assembly of FIGS. 16 and 17, having an elongate neck 74 through which suture 14 is fed from an internal reel, but in this embodiment, the restraining mechanism has an elongated curvilinear stud disposed on the side 126 of the suture reel dispenser, below the neck 74. The elongated stud 124 is integrally formed, preferably in one piece, from a semi-rigid material such as neoprene rubber or a semi-rigid thermoplastic. It has slots 128 and 130 respectively formed into its top and bottom edges to receive top and bottom edges defining an opening 132 through the side wall 126. The stud 124 includes an integrally formed inner, elongated pad 134 having a concave inner surface 136 that is spaced from, but closely adjacent the edge 138 of the suture reel 140, a distance that will not interfere with rotation of the suture reel 140.

In operation, the surgeon withdraws suture 14 from the neck 74 of the dispenser 122, which causes the internal suture reel to rotate on its boss 142 until a desired amount of suture has been obtained. He or she then simply presses the stud 124, which causes the pad 134 to bear against the outer surface 138 of the suture reel 140 to stop its rotation. This will prevent the suture 14 from unwinding as the surgeon pulls on it.

Figure 25:
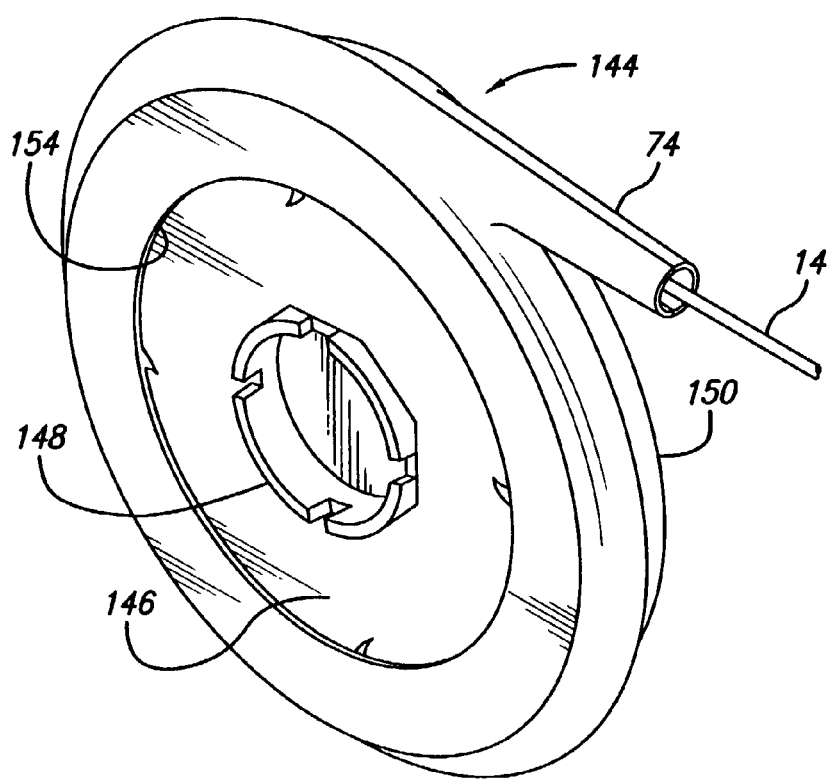
FIG. 25 is a perspective view of a dispenser housing only partially encasing a freely spinning suture reel in accordance with another embodiment of this invention.

Referring to FIG. 25, in another embodiment of the invention, a suture reel dispenser 144 is provided that is partially open. A suture reel 146 is rotatably disposed on a boss 148 carried by a rear wall 150 of the dispenser 144. The dispenser 144 has a front wall 152 formed with an opening 154 sufficiently large to expose the suture reel 146 so that a surgeon can touch the suture reel when he or she desires to stop its rotation, but sufficiently small so that the dispenser 144 can be grasped without touching the suture reel 146. This permits the suture reel 146 to freely rotate or spin when the suture 14 is pulled from the suture reel 146, but stopped by applying finger pressure on the suture reel 146. This is particularly useful when placing the suture 14 around instruments and when tying the suture 14. Moreover, with direct access to the suture reel 146, if too much suture 14 s pulled from the suture reel 146, it can be rotated in the opposite direction in order to rewind the excess suture 14.

Figure 26:
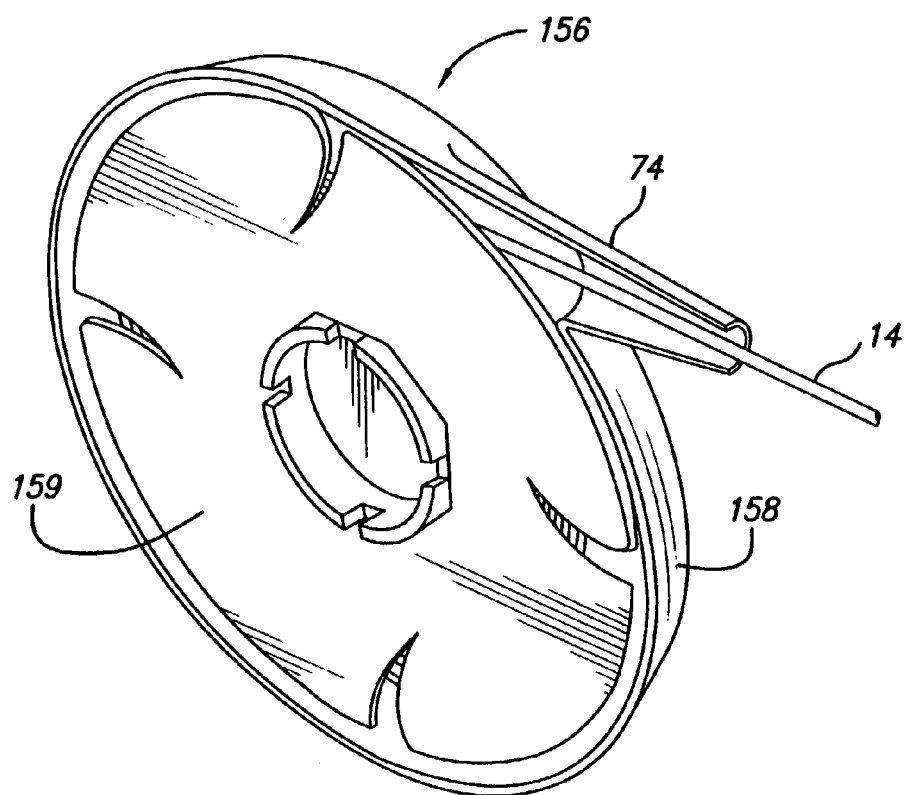
FIG. 26 is a perspective view of a totally open dispenser housing in accordance with another embodiment of this invention, supporting a freely spinning suture reel and having a relatively wide side surface.

Referring to FIG. 26, another embodiment is shown which is similar in construction to the embodiment of FIG. 25, but which is completely open. In this embodiment, the dispenser housing 156 has a relatively wide, circumferential side wall 158, substantially wider than the side wall in the embodiment of FIG. 25, allowing the suture reel to sit at a depth below the side wall 158. The side wall 158 is sufficiently wide to prevent unnecessary touching of the suture reel 159 as suture 14 is pulled from the suture reel 159. The surgeon grasps the dispenser 156, pulling a length of suture 14 from the suture reel, and may stop rotation of the reel by moving his or her finger onto the suture reel 159. For example, while the side wall for the embodiment of a standard dispenser is 3 mm wide, the side wall of this embodiment is at least 5 mm wide.

Figure 27:
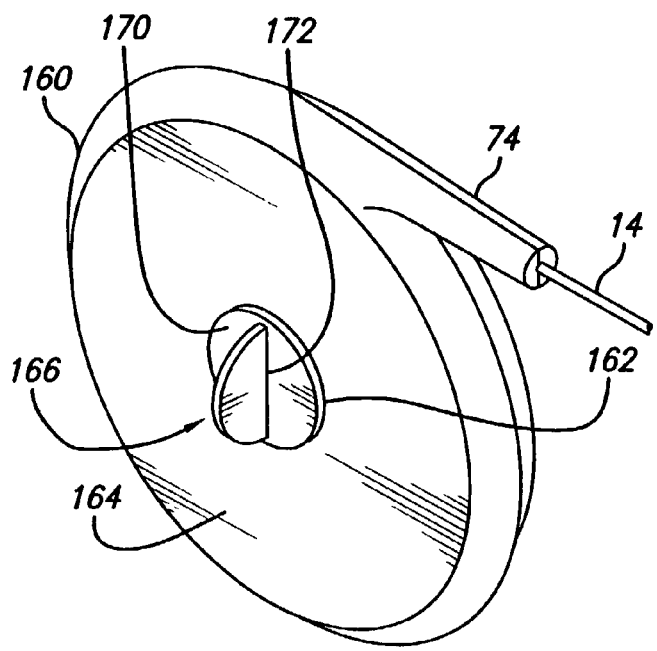
FIG. 27 is a perspective view of an enclosed dispenser housing in accordance with another embodiment of this invention, supporting a rotating suture reel and having a foldable tab grip extending through a central opening in the housing front wall to facilitate retention and rewinding of suture.

Referring to FIG. 27, a dispenser 160 is shown in accordance with another embodiment of the invention. The dispenser 160 is similar in construction to the dispenser 62 of FIGS. 16 and 17, but in place of the land 70 of FIGS. 16 and 17, an opening 162 in that wall 164 is provided. In addition, a foldable tab 166 is connected to the adjacent surface 168 of the enclosed suture reel. The tab 166 can be formed as part of a disk 170, one half of which is glued or otherwise secured to the outer surface of the suture reel wall 168. The tab 166, defined by the other half of the disk, is foldable along a living hinge defined by a line of weakness 172 on the disk 170. By such means, the tab rotates with the suture reel. The tab 166 can be raised in order to facilitate the re-winding of excess suture 14 pulled from the suture reel. When in the lowered position, the tab 166 is out of the user's way. The tab 166 is particularly useful to prevent the suture 14 from unwinding from the suture reel at such times as when tying the suture 14, or when placing the suture 14 around an instrument.

Figure 28:
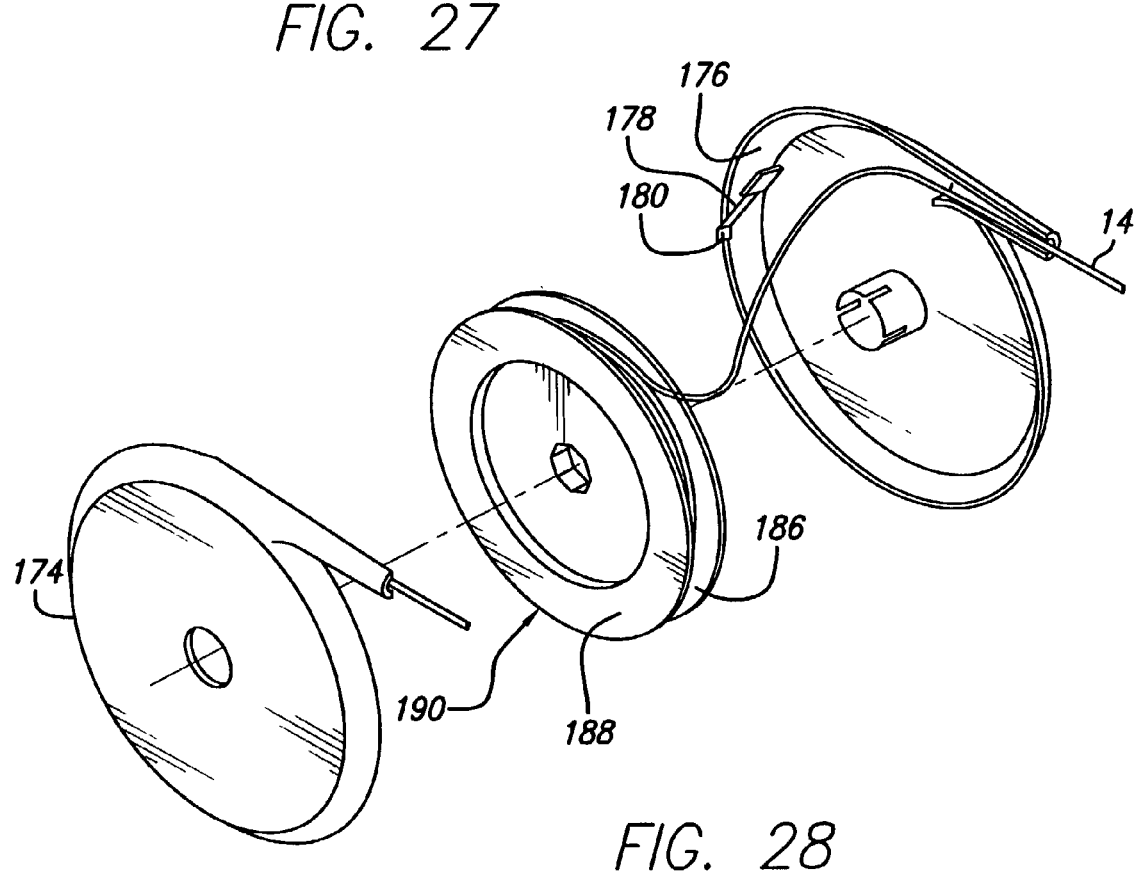
FIG. 28 is an exploded view of enclosed suture reel with sponge mechanism on a suture follower placed within the housing.
Figure 29:
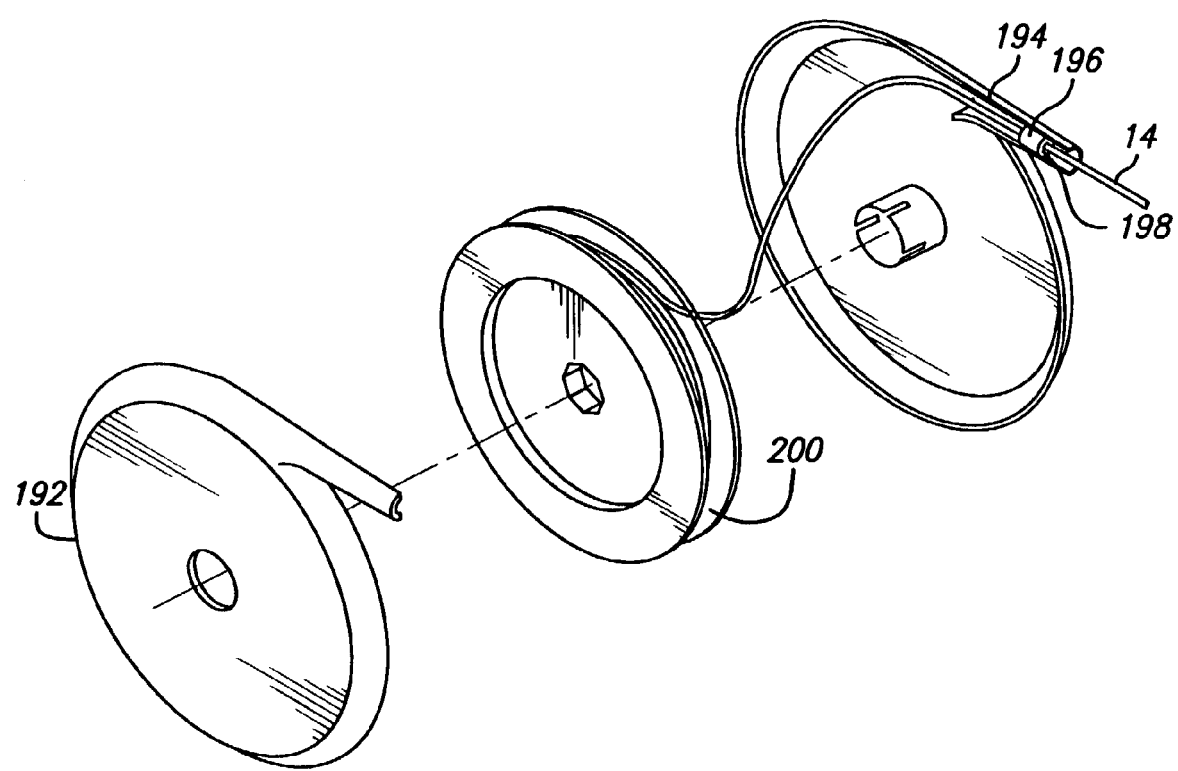
FIG. 29 is an exploded view of enclosed suture reel with sponge mechanism placed within the exit neck of the housing.

Referring to FIG. 28, a dispenser 174 is shown in accordance with another embodiment of the invention. The dispenser 174 is similar in construction to the dispenser 62 of FIGS. 16 and 17, but is provided internally with a mechanism for applying tension to the suture 14. A sponge-like material 176 is carried on the distal end of a cantilever 178 which is secured, e.g., by gluing or welding, or the like, at its proximal end 180 to the inner surface of a side wall 182 of the dispenser. The cantilever is bent adjacent the proximal end so that the sponge-like material serves as a follower cam for the suture 14 wound on the suture reel 184, putting tension downwardly onto the suture reel 184. The sponge-like material 176 is configured so as to readily fit between the opposite walls 186 and 188 of the suture reel 190. The tension should not be sufficient to hinder the free spinning movement of the suture reel 184, but sufficient to keep the sponge-like material 176 in contact with the wound suture 14 When the sponge-like material 176 is impregnated with a suture moistening liquid, e.g., alcohol, it will be in constant contact with the wound suture 14 keeping the suture 14 moist at all times. By using a sponge to apply the moistening liquid, one can decrease the weight of the suture reel, which decreases the amount of shipping cost. Referring to FIG. 29, a dispenser 192 is shown in accordance with another embodiment of the invention. The dispenser 192 is similar in construction to the dispenser 62 of FIGS. 16 and 17, but is provided in its neck 194 with a mechanism for applying tension to the suture 14. A sponge-like material 196 is secured, e.g., by gluing, internally of the neck as a plug, but is formed with an opening 198 through which the suture 14 extends. The sponge-like material fully encloses the suture 14 in order to keep contact with it, but it is not so tight as to prevent the smooth release of the suture 14 from the suture reel. The sponge-like material 196 can be impregnated with a suture moistening liquid, such as that described above, and will be in constant contact with the suture 14 keeping the suture 14 moist at all times. The amount of liquid needed to keep the suture 14 moist will be less than used if the suture is moistened by the present method of applying liquid.

Modifications, and combinations of the foregoing structures can be made. Also, an indicia or label can be engraved or placed on or within the housing mechanism of any of the above mentioned suture reel mechanisms. This indicia or label is used to indicate the size of suture within the suture reel mechanism. This identification system exists within the suture reel mechanisms sold to hospitals today. Without this identification system, the doctors and nurses will not know what size suture 14 is contained within the suture reel dispenser.

I claim:

1. A dispenser for suture, comprising:
   a suture reel on which the suture is wound, the reel being formed with an axle having an outer surface between first and second opposing walls in parallel alignment and spaced from each other to define a housing for the suture reel with a narrow width between the opposing walls, the width being of a dimension to accommodate only a single column of suture wound thereon, and
   a first of said opposing walls being formed with a view window adjacent the outer surface of the axle, the other opposing wall having a different color near the outer surface of the axle than the color on that wall spaced further from said outer axle surface whereby the combination of said narrow width, said view window and said different color near the outer surface of the axle facilitate one to see the end segment of the suture, indicating that the suture is soon to be depleted so that as the suture is unwound one can visually observe that the end of the suture is near.

* * * * *